Figures 1A, 1B, 1C:
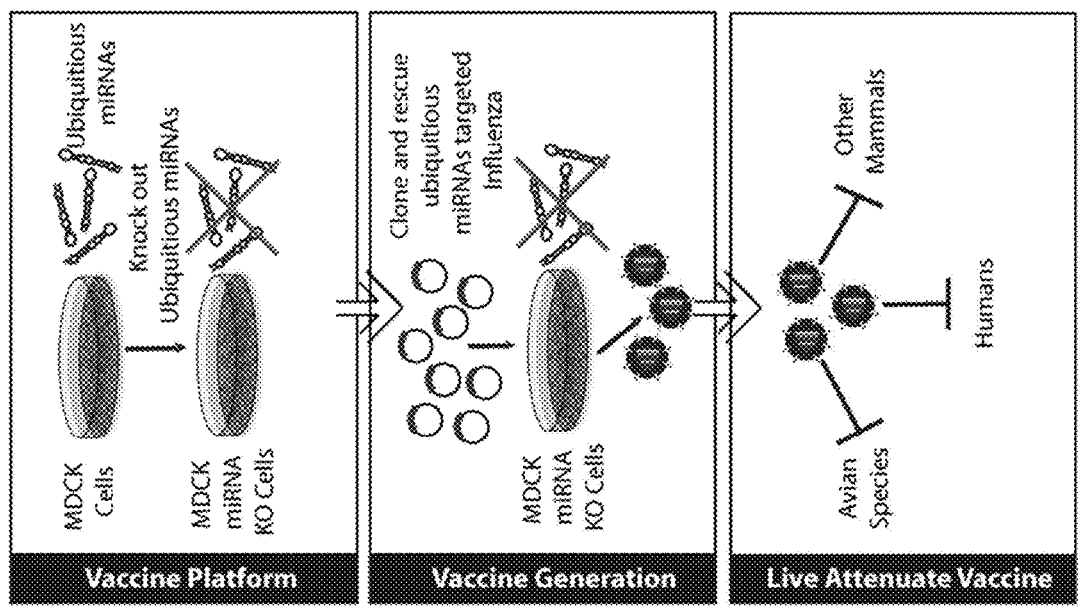

US010086063B2

(12) United States Patent
Langlois et al.

(10) Patent No.: US 10,086,063 B2
(45) Date of Patent: Oct. 2, 2018

(54) METHODS OF MAKING AND USING LIVE ATTENUATED VIRUSES

(71) Applicant: Regents of the University of Minnesota, Minneapolis, MN (US)

(72) Inventors: Ryan Andrew Langlois, Minneapolis, MN (US); Jessica Karen Fiege, Minneapolis, MN (US); Louisa Elizabeth Sjaastad, Minneapolis, MN (US); Barbara Mae Waring, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 15/274,491

(22) Filed: Sep. 23, 2016

(65) Prior Publication Data

US 2017/0080079 A1 Mar. 23, 2017

Related U.S. Application Data

(60) Provisional application No. 62/222,322, filed on Sep. 23, 2015.

(51) Int. Cl.

| | |
|---|---|
| *A61K 48/00* | (2006.01) |
| *C07H 21/04* | (2006.01) |
| *C07H 21/02* | (2006.01) |
| *C12N 15/85* | (2006.01) |
| *A61K 31/7088* | (2006.01) |
| *A61K 39/145* | (2006.01) |
| *C12N 7/00* | (2006.01) |
| *C12N 5/00* | (2006.01) |
| *A61K 39/00* | (2006.01) |

(52) U.S. Cl.
CPC .............. *A61K 39/145* (2013.01); *C12N 5/00* (2013.01); *C12N 7/00* (2013.01); *A61K 2039/5254* (2013.01); *C12N 2501/65* (2013.01); *C12N 2760/16034* (2013.01); *C12N 2760/16062* (2013.01)

(58) Field of Classification Search
CPC ................ A61K 2300/00; A61K 31/22; A61K 31/7088; A61K 38/1709; C12N 2310/32
See application file for complete search history.

(56) References Cited

U.S. PATENT DOCUMENTS

| | | | |
|---|---|---|---|
| 5,453,566 A | | 9/1995 | Shewmaker et al. |
| 6,107,094 A | | 8/2000 | Crooke |
| 6,506,559 B1 | | 1/2003 | Fire et al. |
| 7,056,704 B2 | | 6/2006 | Tuschl et al. |
| 7,078,196 B2 | | 7/2006 | Tuschl et al. |
| 8,883,995 B2 | | 11/2014 | Tenoever |

FOREIGN PATENT DOCUMENTS

| | | | |
|---|---|---|---|
| EP | 2403527 | | 1/2012 |
| WO | WO 2010/101663 | | 9/2010 |
| WO | WO2010101663 | * | 9/2010 |
| WO | WO 2013102155 | * | 7/2013 |

OTHER PUBLICATIONS

Barnes et al., "Harnessing endogenous miRNAs to control virus tissue tropism as a strategy for developing attenuated virusvaccines," *Cell Host Microbe.*, 4(3):239-48, Sep. 11, 2008.
Bartel, "MicroRNA Target Recognition and Regulatory Functions," *Cell.*, 136(2):215-233, Jan. 23, 2009.
Chenna et al., "Multiple sequence alignment with the Clustal series of program," *Nucleic Acids Res.*, 31(13):3497-3500, 2003.
Fodor et al., "Rescue of Influenza A Virus from Recombinant DNA," *J Virol.*, 73(11):9679-9682, Nov. 1999.
Kelly et al, "Engineering microRNA responsiveness to decrease virus pathogenicity," *Nature Medicine.*, 14(11):1278-1283, Nov. 2008.
Langlois et al., "In vivo delivery of cytoplasmic RNA virus-derived miRNAs," *Mol.Therapy.*, 20(2):367-375, Feb. 2012.
Langlois et al., "Hematopoietic-specific targeting of influenza A virus reveals replication requirements for induction of antiviral immune responses," *PNAS.*, 109(30): 12117-12122, Jul. 24, 2012.
Langlois et al., "MicroRNA-based strategy to mitigate the risk of gain-of-function influenza studies," *Nature Biotechnology* 31(9):844-847, Aug. 11, 2013.
Perez et al., "MicroRNA-mediated species-specific attenuation of influenza A virus," *Nature Biotechnology* 27:572-576, 2009.
Pfeffer et al., "Identification of microRNAs of the herpesvirus family," *Nat Methods.*, 2(4):269-276, 2005.
Pham et al., "Replication in Cells of Hematopoietic Origin Is Necessary for Dengue Virus Dissemination," *PLoS Pathogens.*, 8(1):e1002465, 10 pages, Jan. 5, 2012.
Shapiro et al., "Noncanonical cytoplasmic processing of viral microRNAs," *RNA*. 16(11):2068-2074, Nov. 2010.

* cited by examiner

*Primary Examiner* — Barry A Chestnut

(74) *Attorney, Agent, or Firm* — Fish & Richardson P.C.

(57) ABSTRACT

This disclosure provides a platform for making live, attenuated viruses. This disclosure also provides methods of using the live, attenuated viruses.

10 Claims, 4 Drawing Sheets

Specification includes a Sequence Listing.

METHODS OF MAKING AND USING LIVE ATTENUATED VIRUSES

CROSS REFERENCE TO RELATED APPLICATIONS

This application claims the benefit of priority under 35 U.S.C. 119(e) to U.S. Application No. 62/222,322 filed Sep. 23, 2015.

TECHNICAL FIELD

This disclosure generally relates to live attenuated viruses and materials and methods for making such live attenuated viruses.

BACKGROUND

An attenuated vaccine is a live vaccine, which can be contrasted with a killed vaccine. An attenuated vaccine is created by reducing the virulence of a pathogen, or eliminating the virulence of a pathogen under certain conditions. Live attenuated vaccines provide better protection to the host, but safety concerns have limited their use outside of the human population. These concerns are obviated by the materials and methods described herein.

SUMMARY

The methods described herein provide a new platform that includes a cell line deficient in one or more universally expressed miRNAs. The platform described herein allows for the production of live, miRNA-attenuated vaccines that can be safely used, for example, in mammalian and avian species.

In one aspect, a method of making a live, attenuated virus is provided. Such a method generally includes providing a modified virus, wherein the virus has been modified to comprise a miRNA-recognition nucleic acid sequence; culturing the modified virus in a miRNA knock-out cell line, wherein the knock-out cell line comprises a mutation or a transgene that results in the absence of the miRNA that, when present, binds to the miRNA-recognition nucleic acid sequence; and collecting the cultured virus, wherein the cultured virus is annotated when introduced into a cell expressing the miRNA.

Representative miRNAs include, without limitation, miRNA-23, miRNA-24, miRNA-29, miRNA-103, and miRNA-107. Representative viruses include, without limitation, an Influenza B virus, respiratory syncytial virus (RSV), polio virus, West Nile virus, Chikungunya virus, Ebola virus, Lassa virus, Dengue virus, SARS coronavirus, and Middle East Respiratory Syndrome (MERS) coronavirus.

In some embodiments, the modified virus includes one miRNA-recognition nucleic acid sequence. In some embodiments, the modified virus includes a plurality of miRNA-recognition nucleic acid sequences.

In some embodiments, the mutation is an insertion, a deletion, a substitution, or a point mutation. In some embodiments, the transgene encodes at least one inhibitory nucleic acid (e.g., an antisense RNA, a RNAi, or a siRNA).

In another aspect, a live, attenuated virus is provided. In one embodiment, a live, attenuated virus made by the methods described herein is provided. In one embodiment, a live, attenuated virus is provided that includes a miRNA-recognition nucleic acid sequence in its genome.

In still another aspect, a method of vaccinating a subject is provided. Such a method generally includes inoculating the subject with a live, attenuated virus as described herein. Representative subjects include, without limitation, humans, birds, cows, pigs, ferrets, dogs, or cats.

In yet another aspect, an article of manufacture is provided that includes a live, attenuated virus as described herein. In some embodiments, the article of manufacture further includes a knock-out cell line as described herein.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1A is a schematic showing one embodiment of a miRNA-mediated vaccine platform as described herein.

FIG. 1B is a schematic showing one embodiment of vaccine generation as described herein.

FIG. 1C is a schematic showing the attenuated viruses that are produced by the methods described herein.

FIG. 2A is a photograph of a gel showing microRNA-mediated attenuation.

FIG. 2B is a photograph of a gel showing miRNA-mediated attenuation.

FIG. 3A shows CRISPR/Cas-mediated deletion of miR-24 from both loci in chromosomes 1 and 20 in MDCK cells. PCR primers specific for each miR-24 location were used and run on an agarose gel demonstrating deletion of miR-24.

FIG. 3B is a RNA Northern Blot analysis from cells in FIG. 3A that demonstrates loss of miR-24 RNA expression.

DETAILED DESCRIPTION

Vaccines that rely upon live attenuated viruses generally provide better protection to the host and usually do not require booster vaccinations, but safety concerns have limited their use, with the exception of a few instances. The approach described herein is unique in that species-ubiquitous microRNAs can be eliminated from cell lines used to grow and rescue the virus, but the virus contains recognition sequences for miRNAs that are ubiquitously expressed in at-risk species (e.g., the species to be vaccinated). The safety concerns usually associated with the use of live attenuated viruses as vaccines are obviated by the methods described herein because miRNAs are used that are universally expressed, which allows for the use of live attenuated vaccines in animals (e.g., domestic poultry) that have previously been hampered by safety concerns with respect to consuming those animals by humans.

Previous efforts to use miRNAs to generate live attenuated vaccines have taken advantage of the natural disparity in expression that some miRNAs exhibit within vaccine production systems (e.g., chicken eggs or Madin-Darby Canine Kidney (MDCK) epithelial cells) and the desired vaccinated population (e.g., humans). These previous approaches have significant limitations, as there are no miRNAs that are absent from, for example, MDCK cells lines but present at levels abundant enough in humans, at-risk mammals (e.g., canines, swine, felines, cattle), and domesticated avian species to repress, or attenuate, virus replication.

Methods are described herein that allow for recognition sequences for specific miRNAs to be engineered into the genomes of viruses, which can be used to restrict its replication in the presence of the cognate miRNA. FIG. 1 is a schematic showing one embodiment of a miRNA-mediated vaccine platform described herein. FIG. 1A shows that broadly expressed miRNAs can be knocked-out in a virus' host cell, and FIG. 1B is a schematic showing the subsequent generation of live, attenuated viruses, which can be used as vaccines. Specifically, FIG. 1B shows that a miRNA recognition sequence can be incorporated into the virus, and, using the miRNA-mediated vaccine platform shown in FIG. 1A, viral vaccines can be rescued and amplified. As shown in FIG. 1C, the resulting live vaccines are broadly attenuated in, for example, avian and mammalian species including humans.

The methods described herein are useful because they allow for generating live, attenuated viruses that can be used as vaccines in avian or mammalian species without the risk of spread into zoonotic hosts. For example, vaccination of turkeys or chickens with a live, attenuated virus as described herein will not result in infections of humans. In addition, since multiple segments of a virus can be targeted simultaneously, the possibility of reassortment of portions of the genome, which is a critical risk of current live, attenuated vaccine modalities, can be significantly diminished and even prevented by using the methods described herein.

miRNA Knockout Cell Line

A miRNA-mediated vaccine platform as described herein requires a cell line that has been engineered to be deficient in one or more miRNAs (e.g., a miRNA knock-out cell line). Such a cell line must be capable of supporting the life cycle of a virus. To date, it has not been possible to generate a miRNA-targeted virus vaccine that is attenuated in both mammalian and avian species; the platform described herein allows for the development of such vaccines.

MicroRNAs are known in the art and are small regulatory RNAs that control mRNA levels within the cell. MicroRNAs are highly evolutionarily conserved within the animal kingdom. Representative miRNAs include, without limitation, miRNA-23, miRNA-24, miRNA-29, miRNA-103, and/or miRNA-107. In the miRNA-mediated vaccine platform described herein, it is desired that miRNAs that are expressed, e.g., abundantly expressed, e.g., ubiquitously expressed, in mammalian and/or avian species Knock-out cell lines (i.e., cell lines deficient for one or more miRNAs) can be made using materials and methods well known in the art such as, without limitation, nucleases (e.g., CRISPR, TALENs, megaTALs, meganucleases, zinc finger nucleases); antibodies (e.g., Fab, Fab2, chimeric, humanized); or ligands, proteins, drugs, chemicals, or small molecules that competitively bind one or more miRNAs, that downregulate miRNA expression, that increase miRNA degradation, or that cause intracellular depletion (e.g., by secretion) of miRNA. See, for example, Sambrook et al., 1990, Molecular Cloning: A Laboratory Manual, Cold Spring Harbor, N.Y.

A skilled artisan also would appreciate that knock-out cell lines can be made, for example, using a transgene that encodes at least one inhibitory nucleic acid. Inhibitory nucleic acids are known in the art and can correspond to the sequence of the miRNA (e.g., a sense strand) or can be complementary to the sequence of the miRNA (e.g., an antisense strand). Inhibitory nucleic acids are known in the art and include, for example, antisense, RNAi, and siRNA. See, for example, U.S. Pat. Nos. 5,453,566; 6,107,094; 6,506,559; 7,056,704; and 7,078,196.

The use of inhibitory nucleic acids also is referred to as RNA interference (RNAi) or post-transcriptional gene silencing (PTGS), which describes a biological process in which RNA molecules inhibit gene expression, typically by causing the destruction of specific mRNA molecules. Without being bound by theory, it appears that, in the presence of an antisense RNA molecule that is complementary to an expressed message (i.e., a mRNA), the two strands anneal to generate long double-stranded RNA (dsRNA), which is digested into short (<30 nucleotide) RNA duplexes, known as small interfering RNAs (siRNAs), by an enzyme known as Dicer. A complex of proteins known as the RNA Induced Silencing Complex (RISC) then unwinds siRNAs, and uses one strand to identify and thereby anneal to other copies of the original mRNA. RISC cleaves the mRNA within the complementary sequence, leaving the mRNA susceptible to further degradation by exonucleases, which effectively silences expression of the encoding gene.

Several methods have been developed that take advantage of the endogenous machinery to suppress the expression of a specific target gene and a number of companies offer RNAi design and synthesis services (e.g., Life Technologies, Applied Biosystems). The use of RNAi can involve the introduction of long dsRNA (e.g., greater than 50 bps) or siRNAs (e.g., 12 to 23 bps) that have complementarity to the target gene, both of which can be processed by endogenous machinery. Alternatively, the use of RNAi can involve the introduction of a small hairpin RNA (shRNA); shRNA is a nucleic acid that includes the sequence of the two desired siRNA strands, sense and antisense, on a single strand, connected by a "loop" or "spacer" nucleic acid. When the shRNA is transcribed, the two complementary portions anneal intra-molecularly to form a "hairpin," which is recognized and processed by the endogenous machinery.

It would be appreciated that a cell line as described herein can be made deficient for more than one miRNA. For example, in some embodiments, a cell line can be made deficient for at least two or more miRNAs using mutagenesis and/or one or more transgenes. For example, one or more transgenes can be introduced into a cell that encode one or more inhibitory nucleic acids directed toward the same or different miRNAs.

Viruses Modified to Include a miRNA-Recognition Sequence

A miRNA-mediated vaccine platform as described herein also requires a modified virus. A modified virus as described herein includes at least one nucleic acid sequence in its genome that is recognized by at least one miRNA (referred to herein as a "miRNA-recognition nucleic acid sequence," sometimes referred to as a "miRNA target sequence"). Modified viruses as described herein can be made using materials and methods that are well known and routine in the art.

miRNA-recognition sequences would be understood to be a nucleic acid sequence, usually associated with a protein-encoding gene, to which a miRNA nucleic acid binds and directs their post-transcriptional repression. Therefore, a miRNA-recognition nucleic acid sequence typically is complementary to at least a portion of the mature strand of the miRNA (e.g., the strand that is loaded into the RNA-induced silencing complex). Bartel (2009, Cell, 136(2):215-

33), incorporated by reference in its entirety, provides a detailed description of miRNA-recognition sequences and how they can be identified.

As with the knock-out cell lines, it would be appreciated that a modified virus can contain one miRNA-recognition nucleic acid sequence or a plurality of miRNA-recognition nucleic acid sequences. A plurality of miRNA-recognition nucleic acid sequence can include two, three, four, or more miRNA-recognition nucleic acid sequences. A plurality of miRNA-recognition sequences can be the same or different recognition sequences for the same miRNA and/or a plurality of miRNA-recognition sequences can be recognition sequences for a plurality of miRNAs.

Nucleic Acids

Unless otherwise specified, nucleic acids referred to herein can refer to DNA and RNA, and also can refer to nucleic acids that contain one or more nucleotide analogs or backbone modifications. Nucleic acids can be single stranded or double stranded, and linear or circular, both of which usually depend upon the intended use.

As used herein, an "isolated" nucleic acid molecule is a nucleic acid molecule that is free of sequences that naturally flank one or both ends of the nucleic acid in the genome of the organism from which the isolated nucleic acid molecule is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule, discussed in more detail below. In addition, an isolated nucleic acid molecule can include an engineered nucleic acid molecule such as a recombinant or a synthetic nucleic acid molecule.

Nucleic acids can be isolated using techniques well known in the art. For example, nucleic acids can be isolated using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides.

It would be appreciated by the skilled artisan that complementary can refer to, for example, 100% sequence identity between the two nucleic acids. In addition, however, it also would be appreciated by the skilled artisan that complementary can refer to, for example, slightly less than 100% sequence identity (e.g., at least 95%, 96%, 97%, 98%, or 99% sequence identity). In calculating percent sequence identity, two nucleic acids are aligned and the number of identical matches of nucleotides between the two nucleic acids is determined. The number of identical matches is divided by the length of the aligned region (i.e., the number of aligned nucleotides) and multiplied by 100 to arrive at a percent sequence identity value. It will be appreciated that the length of the aligned region can be a portion of one or both nucleic acids up to the full-length size of the shortest nucleic acid. It also will be appreciated that a single nucleic acid can align with more than one other nucleic acid and hence, can have different percent sequence identity values over each aligned region.

The alignment of two or more nucleic acids to determine percent sequence identity can be performed using the computer program ClustalW and default parameters, which allows alignments of nucleic acid sequences to be carried out across their entire length (global alignment). Chenna et al., 2003, Nucleic Acids Res., 31(13):3497-500. ClustalW calculates the best match between a query and one or more subject nucleic acid sequences, and aligns them so that identities, similarities and differences can be determined. Gaps of one or more nucleotides can be inserted into a query sequence, a subject sequence, or both, to maximize sequence alignments. For fast pairwise alignment of nucleic acid sequences, the default parameters can be used (i.e., word size: 2; window size: 4; scoring method: percentage; number of top diagonals: 4; and gap penalty: 5); for an alignment of multiple nucleic acid sequences, the following parameters can be used: gap opening penalty: 10.0; gap extension penalty: 5.0; and weight transitions: yes. ClustalW can be run, for example, at the Baylor College of Medicine Search Launcher website or at the European Bioinformatics Institute website on the World Wide Web.

The skilled artisan also would appreciate that complementary can be dependent upon, for example, the conditions under which two nucleic acids hybridize. Hybridization between nucleic acids is discussed in detail in Sambrook et al. (1989, Molecular Cloning: A Laboratory Manual, 2nd Ed., Cold Spring Harbor Laboratory Press, Cold Spring Harbor, N.Y.; Sections 7.37-7.57, 9.47-9.57, 11.7-11.8, and 11.45-11.57). Sambrook et al. disclose suitable Southern blot conditions for oligonucleotide probes less than about 100 nucleotides (Sections 11.45-11.46). The Tm between a nucleic acid that is less than 100 nucleotides in length and a second nucleic acid can be calculated using the formula provided in Section 11.46. Sambrook et al. additionally disclose Southern blot conditions for oligonucleotide probes greater than about 100 nucleotides (see Sections 9.47-9.54). The Tm between a nucleic acid greater than 100 nucleotides in length and a second nucleic acid can be calculated using the formula provided in Sections 9.50-9.51 of Sambrook et al.

The conditions under which membranes containing nucleic acids are prehybridized and hybridized, as well as the conditions under which membranes containing nucleic acids are washed to remove excess and non-specifically bound probe, can play a significant role in the stringency of the hybridization. Such hybridizations and washes can be performed, where appropriate, under moderate or high stringency conditions. For example, washing conditions can be made more stringent by decreasing the salt concentration in the wash solutions and/or by increasing the temperature at which the washes are performed. Simply by way of example, high stringency conditions typically include a wash of the membranes in 0.2×SSC at 65° C.

In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium. It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane. A nucleic acid molecule is deemed to hybridize to a nucleic acid, but not to another nucleic acid, if hybridization to a nucleic acid is at least 5-fold (e.g., at least 6-fold, 7-fold, 8-fold, 9-fold, 10-fold, 20-fold, 50-fold, or 100-fold) greater than hybridization to another nucleic acid. The amount of hybridization can be quantified directly on a membrane or from an autoradiograph using, for example, a PhosphorImager or a Densitometer (Molecular Dynamics, Sunnyvale, Calif.).

Methods of Making and Using a Live, Attenuated Virus

The cell lines described herein that are deficient in one or more miRNAs can be infected (e.g., transfected) with a modified virus as described herein and used to make live, attenuated viruses, which can be used as vaccines. The relationship that is required between the deficient miRNA(s) in the cell line and the miRNA-recognition nucleic acid sequence would be appreciated by a skilled artisan. That is, the miRNA(s) that are deficient in the knock-out cell line would, in the absence of the deficiency (e.g., in the absence of a mutation(s) or a transgene(s)), recognize the miRNA-recognition nucleic acid sequence that is contained within the modified virus.

The virus cultured can be collected and purified. Viruses can be collected and purified using any number of means and typically includes at least one cell culturing step in a suitable host cell or organism. See, for example, Acheson, 2011, Fundamentals of Molecular Virology, $2^{nd}$ Ed., Wiley & Sons.

A live, attenuated virus vaccine made by the methods described herein can be used to vaccinate a subject. The vaccination of a subject is routine in the art and typically includes inoculating the subject with the vaccine. Inoculation can be orally, rectally, topically, nasally, ocularly, intestinally, parenterally, or via the pulmonary tract. Routes of parenteral inoculation include intravenous, intramuscular, intradermal and subcutaneous administration. It would be appreciated that the live virus vaccine as described herein is attenuated in cells expressing the miRNA(s) (i.e., cells in the subject).

The methods described herein can be used as a platform to generate safe and effective vaccines in any number of subjects. For example, subjects can include mammals (e.g., humans, cattle, swine, ferrets, canines and felines) and avian species (e.g., domestic poultry species such as chickens, turkeys, and ducks).

The platform described herein can be used to produce live, attenuated virus vaccines using virtually any virus. The viruses that can be attenuated using the methods described herein include, without limitation, RNA and DNA viruses, and single-stranded and double-stranded viruses. Non-limiting examples of viruses that can be attenuated using the methods described herein include influenza virus (e.g., Influenza B virus; e.g., H1N1, H2N2, H3N2, H5N1, H5N2, H7N9, and H9N9), respiratory syncytial virus (RSV), polio virus, West Nile virus, Chikungunya virus, Ebola virus, Lassa virus, Dengue virus, SARS coronavirus, and Middle East Respiratory Syndrome (MERS) coronavirus.

It would be appreciated by a skilled artisan that the cell line that is made deficient for one or more miRNAs is limited only by the corresponding virus. That is, the cell line that is made deficient for one or more miRNAs needs to support the complete life cycle of the virus and needs to be able to produce new virions. Cell lines as used herein can be, for example, human pulmonary epithelial cells (A549), canine kidney cells (MDCK), or African green monkey kidney cells (Vero).

Articles of Manufacture

This disclosure also provides for articles of manufacture (e.g., "kits") that contain a live, attenuated virus as described herein. An article of manufacture also can include a corresponding knock-out cell line (e.g., in culture, lyophilized). Additionally, an article of manufacture may further include one or more buffers, adjuvants, or co-factors.

In some embodiments, an article of manufacture can include one or more syringes for delivering a live, attenuated virus as described herein to an individual (e.g., to vaccinate an individual). In some embodiments, a live, attenuated virus can be provided (e.g., packaged) within one or more syringes.

The components of an article of manufacture can be packaged together with suitable packaging materials. Articles of manufacture also can contain a package insert or package label having instructions thereon for using the live, attenuated virus and/or the knock-out cell line.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Small RNA Deep Sequencing microRNAs (miRNAs) were sequenced on the Illumina platform as previously described (Shapiro et al., 2010, RNA 16:2068-74; Pfeffer et al., 2005, Nat Methods, 2:269-76; and Langlois et al., 2013, Nature Biotech., 31:844-7). Briefly, RNA was extracted from the indicated tissue using standard TRIZOL protocols. RNA was run on a 15% denaturing Tris-Urea gel flanked by radiolabeled Decade markers (Ambion). Small RNA species between 15 and 30 nucleotides then were isolated, and the 3' end of the small RNA fraction was ligated to an adapter using the Rnl2 Air™ Ligase (BIOO Scientific). The resulting ligated RNA then was separated from the unligated adapters by gel purification using size to discriminate. The 5' end then was ligated to an adapter RNA oligonucleotide using T4 RNA ligase (NEB).

Following gel isolation, the ligation product was reverse transcribed, PCR amplified (21 cycles) and purified by agarose-based gel electrophoresis. Quality of the small RNA library was assessed on the Agilent 2100 Bioanalyzer (Agilent). RNA libraries were sequenced on the Illumina Platform and mapped to pre-miRNAs as annotated on miRBase (mirbase.org on the World Wide Web). Percent of total was calculated by dividing the indicated miRNA species by the total number of miRBase mapped small RNAs in the library. Families of miRNAs were pooled (e.g., miR-29a, miR-29b-1, miR-29b-2 and miR-29c-1 and miR-29c-2 were combined and designated "miR-29"), since there is a high level of conservation amongst the mature miRNAs produced from families.

Table 1 shows the results from the experiments described herein as well as data provided by Perez et al. (2009, Nature Biotechnol., 27:572-6), Langlois et al. (2012, Mol. Therapy, 20:367-75), Langlois et al. (2012, PNAS, 109:12117-22), and Langlois et al. (2013, Nature Biotechnol., 31:844-7). Table 1 is a heat map showing the amount of various miRNAs (% of total) in humans (A549 cells), ferret (respiratory tract; combined data for nasal, trachea, bronchus and lung parenchyma), canine (MDCK cells), mouse (embryonic fibroblasts), and chicken (embryonic tissue). Table 1 shows that, while there is some heterogeneity in miRNA expression across species, there are several miRNAs that are highly expressed across both species and cell types. Importantly, these miRNAs are expressed in species that are susceptible to influenza virus infection.

TABLE 1

Percent of miRNA Expression

| | Human | Ferret | Canine | Mouse | Chicken |
|---|---|---|---|---|---|
| miR-21 | 43.0 | 2.9 | 38.8 | 10.3 | 2.8 |
| miR-24 | 6 | 3.2 | 3.8 | 3.2 | 11.6 |
| miR-23 | 3.1 | 3.0 | 2.5 | 0.6 | 3.1 |
| miR-103 | 1.4 | 0.3 | 3.2 | 1.3 | 3.1 |
| miR-29 | 6.0 | 1.6 | 4.6 | 6.9 | 1.0 |
| miR-31 | 6.0 | 0 | 5.2 | 5.0 | 0.1 |
| miR-125 | 1.8 | 3.8 | 1.7 | 0.7 | 0 |

Example 2—Western Blotting

The indicated MDCK cells were infected with wild type control or targeted influenza viruses at a multiplicity of infection of one. 24 hours post-infection, protein was harvested using a NP40 lysis buffer and run on a 4-15% gradient gel (BioRad). Protein was transferred to nitrocellulose blocked in 5% milk and probed using anti mouse NP antibody (NR43899 Bei resources) or anti sera from H7 HA immunized mice (gift from Dr. Peter Palese and Dr. Rong Hai, MSSM). Actin (anti mouse Pan Actin; Neomarkers) was used as a loading control. Protein was then revealed using anti mouse secondary antibodies conjugated to HRP (Roche).

Figure 2A:
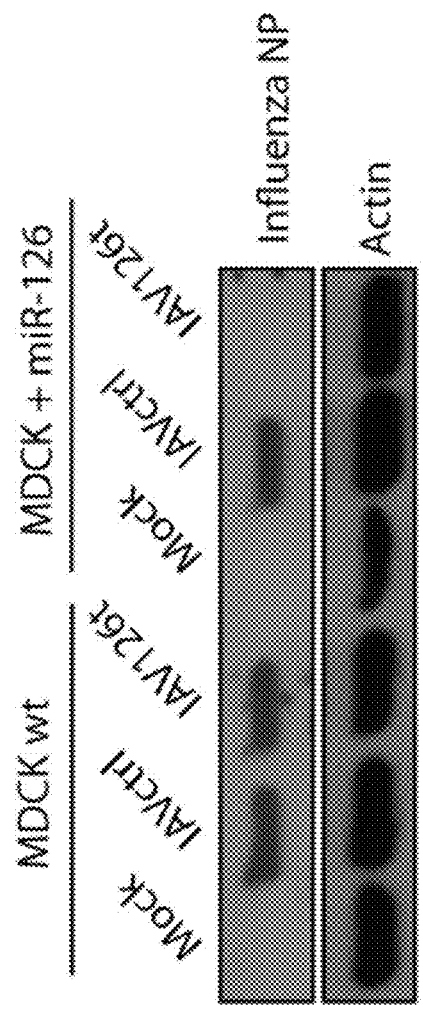
Figure 2B:
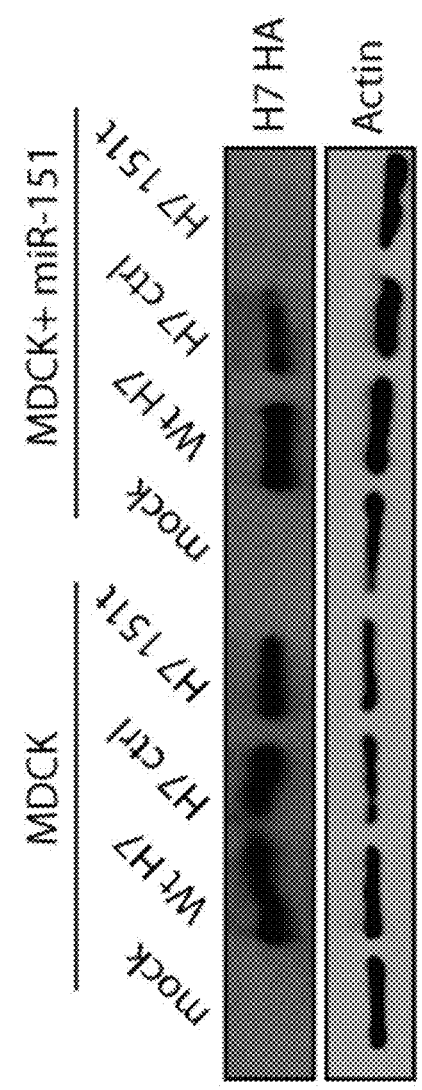
Figure 3A:
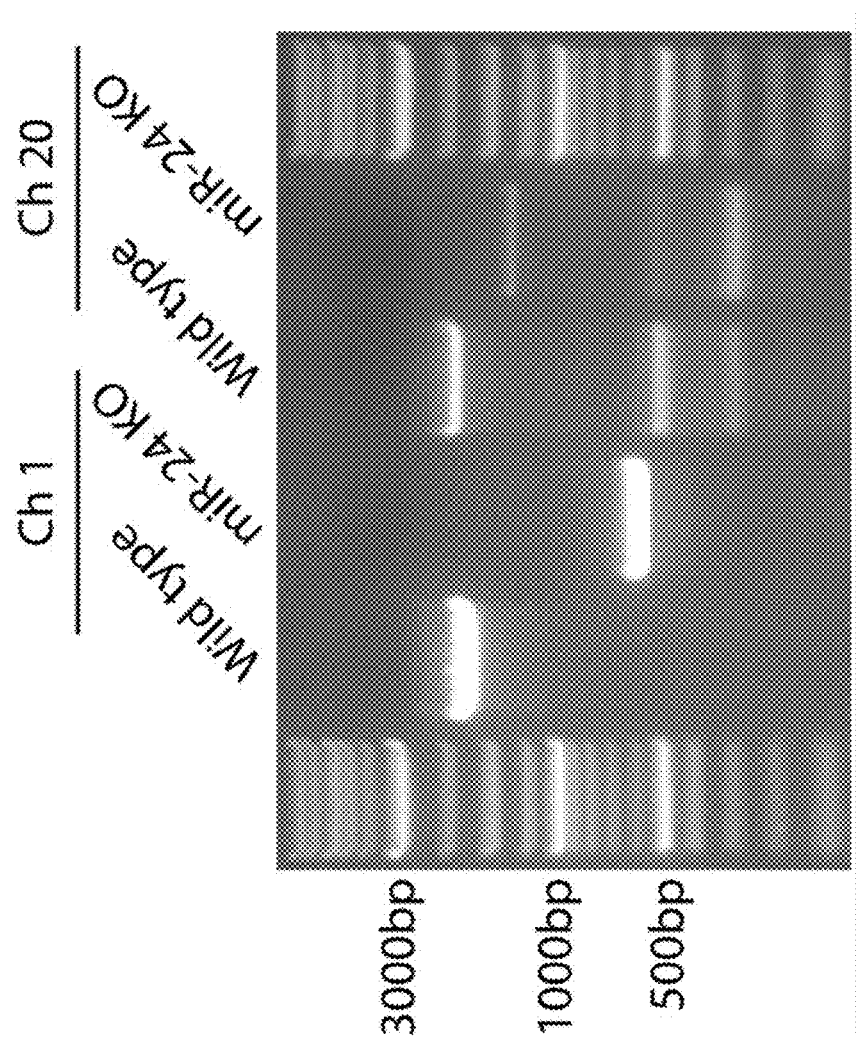
Figure 3B:
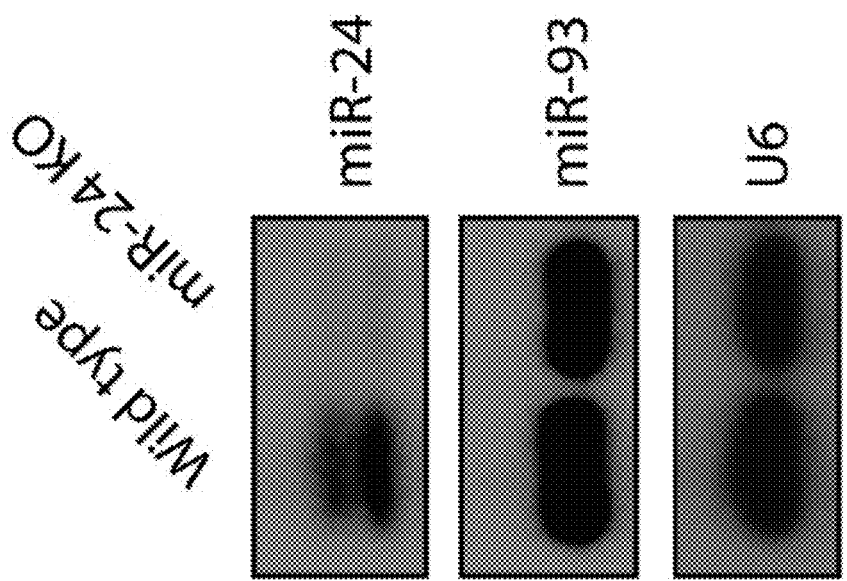

The Western blots are shown in FIG. 2. MDCK cells lacking miR-126 (FIG. 2A) and miR-151 (FIG. 2B) were engineered to express these miRNAs. Influenza viruses were then generated with miR-126 recognition sites (CGC AUU AUU ACU CAC GGU ACG A (SEQ ID NO:1)) incorporated into NP (FIG. 2A) or miR-151 recognition sites (ACU AGA CUG UGA GCU CCU CGA (SEQ ID NO:2)) incorporated into H7 HA (FIG. 2B) (see Example 3 below). Wild type MDCK or miRNA-expressing MDCK cells were then infected and probed for targeted protein production. FIGS. 2A and 2B show that insertion of miRNA recognition sites in either the NP or the HA gene resulted in attenuated virus replication in the presence of the cognate miRNA but not in the absence of the cognate miRNA.

Example 3—Generation of Recombinant miRNA-Targeted Influenza Viruses miRNA-targeted recombinant influenza viruses were generated using the eight plasmid standard reverse genetics system (Fodor et al., 1999, J. Virol., 73:9679-82; and Langlois et al., 2013, Nature Biotech., 31:844-7). Four perfectly complementary recognition sites were cloned using overlapping PCR or synthesized by Genewiz. To allow for insertion into the influenza genome without disrupting the coding sequence of the protein or the packaging signals of the viral RNA, the complete packaging signal 200 base pairs from the 5' end of the vRNA was duplicated and added at the end of the stop codon. A unique restriction site was added, allowing for insertion of the targeting sequence using infusion cloning systems (Clontech). The targeted plasmid was then used with 7 plasmids from unmanipulated segments to rescue virus in 293 cells. Virus was then plaque purified and amplified in 10-day old embryonated chicken eggs.

Example 4—Generation of miRNA Knock-Out Cells miRNA knockout cells are generated by designing and transfecting guide RNAs flanking the 5' and 3' ends of the primary miRNA in the genome. Cells are co-transfected with a plasmid expressing the nuclease as well as the cognate miRNA-targeted virus. Cells are clonally selected and the loss of miRNA locus is confirmed by PCR and small RNA Northern blot analysis. MicroRNA targeted virus is inserted after the stop codon and upstream of a complete packaging signal. These viruses then are rescued and amplified in the miRNA knockout cell lines.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of delivering a live, attenuated viral vaccine to a subject, comprising:
providing a genetically-engineered virus, wherein the virus has been genetically-engineered to comprise a miRNA-21-recognition nucleic acid sequence to which miRNA-21 binds;
culturing the genetically-engineered virus in a cell line that has been genetically-engineered to knock-out expression of the endogenous miRNA-21, thereby producing a live, attenuated viral vaccine; and
delivering the live, attenuated viral vaccine to a subject, wherein the subject comprises cells that endogenously express miRNA-21.

2. The method of claim 1, wherein the genetically-engineered virus comprises one miRNA-recognition nucleic acid sequence.

3. The method of claim 1, wherein the genetically-engineered virus comprises a plurality of miRNA-recognition nucleic acid sequences.

4. The method of claim 1, wherein the virus is an Influenza B virus, respiratory syncytial virus (RSV), polio virus, West Nile virus, Chikungunya virus, Ebola virus, Lassa virus, Dengue virus, SARS coronavirus, and Middle East Respiratory Syndrome (MERS) coronavirus.

5. The method of claim 1, wherein the cell line that has been genetically-engineered to knock-out expression of the endogenous miRNA-21 comprises a mutation.

6. The method of claim 1, wherein the cell line that has been genetically-engineered to knock-out expression of the endogenous miRNA-21 comprises a transgene.

7. The method of claim 6, wherein the transgene encodes at least one inhibitory nucleic acid.

8. The method of claim 7, wherein the at least one inhibitory nucleic acid is an antisense RNA, a RNAi, or a siRNA.

9. The method of claim 1, wherein the subject is a human, a bird, a cow, a pig, a ferret, a dog, or a cat.

10. The method of claim 5, wherein the mutation is an insertion, a deletion, a substitution, or a point mutation.

* * * * *

SEQUENCE LISTING

<160> NUMBER OF SEQ ID NOS: 2

<210> SEQ ID NO 1
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 1
cgcauuauua cucacgguac ga                                           22

<210> SEQ ID NO 2

```
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 2
acuagacugu gagcuccucg a                                                    21
```